US006025338A

United States Patent [19]

Barbet et al.

[11] Patent Number: 6,025,338
[45] Date of Patent: *Feb. 15, 2000

[54] NUCLEIC ACID VACCINES AGAINST RICKETTSIAL DISEASES AND METHODS OF USE

[75] Inventors: Anthony F. Barbet, Archer; Roman Reddy Ganta; Michael J. Burridge, both of Gainesville, all of Fla.; Suman M. Mahan, Harare, Zimbabwe

[73] Assignee: University of Florida, Gainesville, Fla.

[ * ] Notice: This patent issued on a continued prosecution application filed under 37 CFR 1.53(d), and is subject to the twenty year patent term provisions of 35 U.S.C. 154(a)(2).

[21] Appl. No.: 08/733,230

[22] Filed: Oct. 17, 1996

[51] Int. Cl.[7] .......................... C12N 15/00; A61K 31/70; A61K 45/00

[52] U.S. Cl. ......................... 514/44; 536/23.1; 435/320.1

[58] Field of Search ................................. 536/23.5, 23.2, 536/23.1; 514/44; 424/184.1, 234.1; 435/320.1, 362, 235.1, 265.1, 269.1; 935/19, 22

[56] References Cited

U.S. PATENT DOCUMENTS

| | | |
|---|---|---|
| 4,879,213 | 11/1989 | Fox et al. . |
| 5,643,578 | 7/1997 | Robinson et al. . |
| 5,783,441 | 7/1998 | Carl et al. . |

FOREIGN PATENT DOCUMENTS

| | | |
|---|---|---|
| WO 9012030 | 10/1990 | WIPO . |

OTHER PUBLICATIONS

Lazar et al (1988) Mol. & Cell. Biol. vol. 8(3), 1247–1252.
Burgess et al (1990) J. Cell. Biol. vol. 111, 2129–2138.
Ulmer et al (Sep. 1996) ASM News vol. 62(9), 476–479.
Sumner et al (1995) Vaccine. vol. 13(1), 29–35.
DuPlessis, J.L. (1970) "Immunity In Heartwater: I. A Preliminary Note On The Role Of Serum Antibodies" Onderstepoort J. vet Res. 37(3):147–150.
Uilenberg, Gerrit (1983) "Heartwater (Cowdria ruminantium Infection): Current Status" Advances in Veterinary Science and Comparative Medicine 27:427–480.
Vishwanath, Suryanarayanan, Gregory A. McDonald, Nancy G. Watkins (1990) "A Recombinant *Rickettsia conorii* Vaccine Protects Guinea Pigs from Experimental Boutonneuse Fever and Rocky Mountain Spotted Fever" Infection and Immunity 58(3):646–653.

van Vliet, A., F. Jongejan, M. vanKleef, B. Zeijst van der (1994) "Molecular Cloning Sequence Analysis, and Expression of the Gene Encoding the Immunodominant 32–Kilodalton Protein of *Cowdria ruminantium*" Infection and Immunity 62(4):1451–1456.

Ulmer, J.B., et al. (1993) "Heterologous Protection Against Influenza by Injection of DNA Encoding a Viral Protein" Science 259:1745–1749.

Schödel, M.–T. Aguado, P.–H. Lambert (1994) "Introduction: Nucleic Acid Vaccines, WHO, Geneva, May 17–18, 1994" Vaccine 12(16):1491–1492.

Sedegah, Martha, Richard Hedstrom, Peter Hobart, Stephen L. Hoffman (1994) "Protection against malaria by immunization with plasmid DNA encoding circumsporozoite protein" Proc. Natl. Acad. Sci. USA 91:9866–9870.

Cox, J.M. Graham, Tim J. Zamb, Lorne A. Babiuk (1993) "Bovine Herpesvirus 1: Immune Responses in Mice and Catle Injected with Plasmid DNA" Journal of Virology 67(9):5664–5667.

McGuire, Travis. C., Edward B. Stephens, Guy H. Palmer, Terry F. McElwain, Carol A. Lichtensteiger, Steve R. Lieb, Anthony F. Barbet (1994) "Recombinant vaccinia virus expression of *Anaplasma marginale* surface protein MSP–1A: effect of promoters, lead sequences and GPI anchor sequence on antibody response" Vaccine 12(5):465–471.

Mahan, S.M., T.C. McGuire, S.M. Semu, M.V. Bowie, F. Jongejan, F.R. Rurangirwa, A.F. Barbet (1994) "Molecular cloning of a gene encoding the immunogenic 21 kDa protein of *Cowdria ruminantium*," *Microbiology* 140:2135–2142.

G. Roman Reddy, C.R. Sulsona, R.H. Harrison, S.M. Mahan, M.J. Burridge, A.F. Barbet (1996) "Sequence Heterogeneity of the Major Antigenic Protein 1 Genes from *Cowdria ruminantium* Isolates from Different Geological Areas," *Clin. Diag. Lab. Immun.* 3(4):417–422.

S.M. Oberle, A.F. Barbet (1993) "Derivation of the complete msp4 gene sequence of *Anaplasma marginale* without cloning," *Gene* 136:291–294.

*Primary Examiner*—Marianne P. Allen
*Attorney, Agent, or Firm*—Saliwanchik, Lloyd & Saliwanchik

[57] ABSTRACT

Described are nucleic acid vaccines containing MAP1-related genes to protect animals or humans against rickettsial diseases.

3 Claims, 3 Drawing Sheets

FIG. 1A

```
C.r.  ATGAATTGCAAGAAAATTTTA------------TCACAAGTACACTAATATCATTAGTG
E.c.  ATGAATTACAAAAAAAGTTCA------------TAACAGCG-ATTGATATCATTAATA
A.m.  ATGAATTACAGAGAATTGTTTACAGGGGCCTG-TCAGCAGCC-ACAGTCTGCGCCTGCT
      ******* **           **     *  *   * **     *

C.r.  TCATTTT---TACCTGGTGTGTCCTTTTCTGATGTAATACAGGAAGACAGCAACCCAGCAG
E.c.  TCCTTCTCTTACCTGGAGTATCATTTCCGACCCAAGGCAGGTAGTGGTCA---TTAACG
A.m.  CCCTACTTGTTAGTGGGGCCGTAGTGCATCTCCCATGAGTCACGAAGTGGCTTCTGAAG
      *  * * ****   *  *  * *                                  *

C.r.  GCAGTGTTTACATTAGCGCAAAATACATGCCAACTGCATCACATTTGGTAAAATGTCAA
E.c.  GTAATTCTACATCAGTGGAAAATACAACAGTTGGAGTGTTTGGACTGGAGTATTCTCTG
A.m.  GGGGAGTAATGGGAGGTAGCTTTTACGTGGTGCGGCCT-ACAGCCCAGCATTTCCTTCT
       *      *  **   *    *     *   *  **         *

C.r.  TCAAAGAAGATTCAAAAAATACTCAAACGGTATTTGGTCTAAAAAAAGATTGGGATGCG
E.c.  CTAAGGAAGAAAGAAATACAACAGTTGGAGTGTTTGGACTGGACAAAATTGGGACGGAA
A.m.  GTTACCTCGTTCGACATGCGTGAGTCAAGCAAAGAGACCTCA--TACGTTAGAGGCTATG
         *   *   *  *   *      *       *   * * * *

C.r.  TTAAAACACCACCATCAGATTCTAGCAATACTAATTCTACAATTTTTACTGAAAAAGACTATT
E.c.  GCGCAATATC--CAACTCCTCCCCAAACGA------TGTATTCACTGTCTCAAATTATT
A.m.  ACAAGAGCATTGCAACGATTGATGTGAGTGTGCCAGCAAACTTTCCAAATCTGGCTACA
                *    *       *                  *              **

C.r.  CTTTCAGATATGAAAACAATCCGTTTTTAGGTTTCGCTGGAGCAATTGGGTACTCAATGA
E.c.  CATTTAAATATGAAAACAACCCGTTTTTAGGTTTTGCAGGAGCTATTGGTTACTCAATGG
A.m.  CTTTGCCTTCTCTAAAAACTTAATCACGTCTTTCGACGGCGTCTTTGGGATATTCTTGG
        **   * *    *** * * *  **   ** ** ** * ** * ***  * ***
```

FIG. 1B

```
C.r.  ATGGACCAAGAATAGAGTTCGAAGTATCCTATGAAACTTTGATGTAAAAAACCTAGGTG
E.c.  ATGGTCCAAGAATAGAGTTCAAGCTTGAAGTATCTTATGAAACATTTGATGTAAAAATCAAGGTA
A.m.  GAGGAGCCAGAGTGGAATTGGAAGCGAGCTACAGAAGTTTGCTACTTTGGCGACGGGC
      **  *  ****  *  **  ****    *    **  *  ****    *

C.r.  GCAACTATAAAACAACGCACACATGTACTGTGCTTTAGATACAGCAGCACAAAATAGCA
E.c.  ACAATTATAAGAATGAAGCACATAGATATTGTGCTCTATCCCATAACTCAGCAGCAGACA
A.m.  AGTACGCAAAAGTG----------GTGCGGAATCTCTGGCAGCTATTACCCGCG
      *      *                 ****    *

C.r.  CTTAATGGCGCAGGATTAACTACACTCTGTTATGGTAAAAAACGAAAATTAACAAATATAT
E.c.  TGAGTAGTGCAAG---TAATAATTTGTCTTTCTAAAAATGAAGGATTACTTGACATAT
A.m.  ACGCTAACATTACTGAGACCAATTACTTCGTAGTAGTCAAGTTCAAAATTGATGAAATCACAAAACCT
      *    *    **    *  *  *  ****  *    *  *  ***

C.r.  CATTAATGTTAAATGCGTGTTATGATATCATGCTTGATGGAATACCAGTTTCTCCATATG
E.c.  CATTTATGCTGAACGCATGCTATGACGTAGTAGGCGAAGGCATACCTTTTTCTCCTTATA
A.m.  CAGTCATGTTAAATGGCTGCTATGAGCGATTTACCTGTCCCGTATG
      **  ****  *  **  ****  *    ****  *    ****

C.r.  TATGTGCAGGTATTGGCACTGACTTAGTGTCAGTAATTAATGCTACAAATCCTAAATTAT
E.c.  TATGCGCAGGTATCGGTTACTGATTTAGTATCCATGTTTGAAGCTACAAATCCTAAAATTT
A.m.  TATGTGCCGGGATAGGCGCAAGCTTTGTTGACATCTCTAAGCAAGTAACCACAAAGCTGG
      ****  *  *  **  *  *    **  *    **    ***

C.r.  CTTATCAAGGAAAGCTAGGCATAAGTTACTCAATCAATTCTGAAGCTTCTATCTTTATCG
E.c.  CTTACCAAGGAAAGTTAGGTTAAGCTACTCTATAAGCCCAGAAGCTTCTGTGTTTATTG
A.m.  CCTACAGGGGCAAGGTTGGGATTAGTTACCAGTTTACTCCGGAATATCCGTTACTGGCAG
      *  *  ****  *  *  ****    *    *  *    *    *

```
C.r. GTGGACATTCCCATAGAGTTATAGGTAATGAATTTAAAGATATATTGCTACCTTAAAAATAT
E.c. GTGGGCACTTCATAAGGTATAAGGTAATAGGAACGAATTTAGAGATATTCCTACTATAATACCTA
A.m. GTGGGTTCTACCACGGGCTATTTGATGAGTCTTACAAGGACATTCCCGCACACAACAGTG
     ****  *    *   **   *  *  * *** ** *        *

C.r. TTACTTCAAAACAGGAATATCTAATCCCTGGCTTTGCATCAGCAACACTTGATGTTTGTC
E.c. CTGGATCAACACTTGCAGGAAAAGGAAACTACCCTGCAATAGTAATACTGGATGTATGCC
A.m. TAAAGTTCTCTGAGAACAAAA------GCCTCAGTCAAAGCGCATATTGCTG
        *        *    *    *         **   *    **  * **  **

C.r. ACTTTGGTATAGAAATTGGGAGGAAGGTTTGTATTTTAA---
E.c. ACTTTGGAATAGAAATGGGAGGAAGGTTTAA--------
A.m. ACTACGGCTTTAACCTTGGAGCAAGATTCCTGTTCAGCTAA
     ***  **   *  *  * **** ***  ***
```

C.r.
E.c.
A.m.

C.r.
E.c.
A.m.

C.r.
E.c.
A.m.

NUCLEIC ACID VACCINES AGAINST RICKETTSIAL DISEASES AND METHODS OF USE

This invention was made with government support under USAID Grant No. LAG-1328-G-00-3030-00. The government has certain rights in this invention.

DESCRIPTION

TECHNICAL FIELD

This invention relates to nucleic acid vaccines for rickettsial diseases of animals, including humans.

BACKGROUND OF THE INVENTION

The rickettsias are a group of small bacteria commonly transmitted by arthropod vectors to man and animals, in which they may cause serious disease. The pathogens causing human rickettsial diseases include the agent of epidemic typhus, *Rickettsia prowazekii*, which has resulted in the deaths of millions of people during wartime and natural disasters. The causative agents of spotted fever, e.g., *Rickettsia rickettsii* and *Rickettsia conorii*, are also included within this group. Recently, new types of human rickettsial disease caused by members of the tribe Ehrlichiae have been described. Over 400 cases of human ehrlichiosis, including some fatalities, caused by *Ehrlichia chaffeensis* have now been reported. Clinical signs of human ehrlichiosis are similar to those of Rocky Mountain spotted fever, including fever, nausea, vomiting, headache, and rash.

Heartwater is another infectious disease caused by a rickettsial pathogen, namely *Cowdria ruminantium*, and is transmitted by ticks of the genus Amblyomma. The disease occurs throughout most of Africa and has an estimated endemic area of about 5 million square miles. In endemic areas, heartwater is a latent infection in indigenous breeds of cattle that have been subjected to centuries of natural selection. The problems occur where the disease contacts susceptible or naive cattle and other ruminants. Heartwater has been confirmed to be on the island of Guadeloupe in the Caribbean and is spreading through the Caribbean Islands. The tick vectors responsible for spreading this disease are already present on the American mainland and threaten the livestock industry in North and South America.

In acute cases of heartwater, animals exhibit a sudden rise in temperature, signs of anorexia, cessation of rumination, and nervous symptoms including staggering, muscle twitching, and convulsions. Death usually occurs during these convulsions. Peracute cases of the disease occur where the animal collapses and dies in convulsions having shown no preliminary symptoms. Mortality is high in susceptible animals. Angora sheep infected with the disease have a 90% mortality rate while susceptible cattle strains have up to a 60% mortality rate.

If detected early, tetracycline or chloramphenicol treatment are effective against rickettsial infections, but symptoms are similar to numerous other infections and there are no satisfactory diagnostic tests (Helmick, C., K. Bernard, L. D'Angelo [1984] *J. Infect. Dis.* 150:480).

Animals which have recovered from heartwater are resistant to further homologous, and in some cases heterologous, strain challenge. It has similarly been found that persons recovering from a rickettsial infection may develop a solid and lasting immunity. Individuals recovered from natural infections are often immune to multiple isolates and even species. For example, guinea pigs immunized with a recombinant *R. conorii* protein were partially protected even against *R. ricketsii* (Vishwanath, S., G. McDonald, N. Watkins [1990] *Infect. Immun.* 58:646). It is known that there is structural variation in rickettsial antigens between different geographical isolates. Thus, a functional recombinant vaccine against multiple isolates would need to contain multiple epitopes, e.g., protective T and B cell epitopes, shared between isolates. It is believed that serum antibodies do not play a significant role in the mechanism of immunity against rickettsia (Uilenberg, G. [1983] *Advances in Vet. Sci. and Comp. Med.* 27:427-480; Du Plessis, Plessis, J. L. [1970] *Onderstepoort J. Vet. Res.* 37(3):147–150).

Vaccines based on inactivated or attenuated rickettsiae have been developed against certain rickettsial diseases, for example against *R. prowazekii* and *R. rickettsii.* However, these vaccines have major problems or disadvantages, including undesirable toxic reactions, difficulty in standardization, and expense (Woodward, T. [1981] "Rickettsial diseases: certain unsettled problems in their historical perspective," In *Rickettsia and Rickettsial Diseases,* W. Burgdorfer and R. Anacker, eds., Academic Press, New York, pp. 17–40).

A vaccine currently used in the control of heartwater is composed of live infected sheep blood. This vaccine also has several disadvantages. First, expertise is required for the intravenous inoculation techniques required to administer this vaccine. Second, vaccinated animals may experience shock and so require daily monitoring for a period after vaccination. There is a possibility of death due to shock throughout this monitoring period, and the drugs needed to treat any shock induced by vaccination are costly. Third, blood-borne parasites may be present in the blood vaccine and be transmitted to the vaccinates. Finally, the blood vaccine requires a cold chain to preserve the vaccine.

Clearly, a safer, more effective vaccine that is easily administered would be particularly advantageous. For these reasons, and with the advent of new methods in biotechnology, investigators have concentrated recently on the development of new types of vaccines, including recombinant vaccines. However, recombinant vaccine antigens must be carefully selected and presented to the immune system such that shared epitopes are recognized. These factors have contributed to the search for effective vaccines.

A protective vaccine against rickettsiae that elicits a complete immune response can be advantageous. A few antigens which potentially can be useful as vaccines have now been identified and sequenced for various pathogenic rickettsia The genes encoding the antigens and that can be employed to recombinantly produce those antigen have also been identified and sequenced. Certain protective antigens identified for *R. rickettsii, R. conorii,* and *R. prowazekii* (e.g. rOmpA and rOmpB) are large (>100 kDa), dependent on retention of native conformation for protective efficacy, but are often degraded when produced in recombinant systems. This presents technical and quality-control problems if purified recombinant proteins are to be included in a vaccine. The mode of presentation of a recombinant antigen to the immune system can also be an important factor in the immune response.

Nucleic acid vaccination has been shown to induce protective immune responses in non-viral systems and in diverse animal species (Special Conference Issue, WHO meeting on nucleic acid vaccines [1994] *Vaccine* 12:1491). Nucleic acid vaccination has induced cytotoxic lymphocyte (CIL), T-helper 1, and antibody responses, and has been shown to be protective against disease (Ulmer, J., J. Donelly, S. Parker et al. [1993] *Science* 259:1745). For example, direct intramuscular injection of mice with DNA encoding the influenza nucleoprotein caused the production of high titer antibodies, nucleoprotein-specific CTLs, and protection against viral challenge. Immunization of mice with plasmid DNA encoding the *Plasmodium yoelii* circumsporozoite protein induced high antibody titers against malaria sporozoites and CTLs, and protection against challenge infection (Sedegah, M., R. Hedstrom, P. Hobart, S. Hoffman [1994] *Proc. Natl. Acad. Sci. USA* 91:9866). Cattle immunized with plasmids encoding bovine herpesvirus 1 (BHV-1) glycoprotein IV developed neutralizing antibody and were partially protected (Cox, G., T. Zamb, L. Babiuk [1993] *J. Virol* 67:5664). However, it has been a question in the field of immunization whether the recently discovered technology of nucleic acid vaccines can provide improved protection against an antigenic drift variant. Moreover, it has not heretofore been recognized or suggested that nucleic acid vaccines may be successful to protect against rickettsial disease or that a major surface protein conserved in rickettsia was protective against disease.

BRIEF SUMMARY OF THE INVENTION

Disclosed and claimed here is a novel vaccine for conferring immunity to rickettsia infection, including *Cowdria ruminantium* causing heartwater. Also disclosed are novel nucleic acid compositions and methods of using those compositions, including to of confer immunity in a susceptible host.

The subject invention concerns a nucleic acid, e.g., DNA or mRNA, vaccine containing the major antigenic protein 1 gene (MAP 1) of rickettsial pathogens driven by the human cytomegalovirus (HCMV) enhancer-promoter. In studies immunizing mice by intramuscular injection of a DNA vaccine composition according to the subject invention, up to 75% of the immunized mice seroconverted and reacted with MAP1 in antigen blots. Splenocytes from immunized mice, but not from control mice immunized with vector only, proliferated in response to recombinant MAP1 and rickettsial antigens in in vitro lymphocyte proliferation tests. In experiments testing different DNA vaccine dose regimens, increased survival rates as compared to controls were observed on challenge with rickettsia Accordingly, the subject invention concerns the discovery that the gene encoding the MAP1 protein can induce protective immunity as a nucleic acid vaccine against rickettsial disease or death resulting therefrom.

BRIEF DESCRIPTION OF THE DRAWING

FIGS. 1A–1C show a comparison of the amino acid sequences from alignment of the three rickettsial proteins, namely, *Cowdria ruminantium* (Cr.), *Ehrlichia chaffeensis* (E.c.), and *Anaplasma marginale* (A.m.). (SEQ ID NOS: 1,3, and 5.)

BRIEF DESCRIPTION OF THE SEQUENCES

SEQ ID NO. 1 is the coding sequence of the MAP1 gene from *Cowdria ruminantium* (Highway isolate).

SEQ ID NO. 2 is the polypeptide encoded by the polynucleotide of SEQ ID NO. 1.

SEQ ID NO. 3 is the coding sequence of the MAP1 gene from *Ehrlichia chaffeensis*.

SEQ ID NO. 4 is the polypeptide encoded by the polynucleotide of SEQ ID NO. 3.

SEQ ID NO. 5 is the *Anaplasma marginale* MSP4 gene coding sequence.

SEQ ID NO. 6 is the polypeptide encoded by the polynucleotide of SEQ ID NO. 5.

DETAILED DISCLOSURE OF THE INVENTION

The subject invention concerns a novel strategy, termed nucleic acid vaccination, for eliciting an immune response protective against rickettsial disease. The subject invention also concerns novel compositions that can be employed according to this novel strategy for eliciting a protective immune response. According to the subject invention, recombinant plasmid DNA or mRNA encoding an antigen of interest is inoculated directly into the human or animal host where the antigen is expressed and an immune response induced. Advantageously, problems of protein purification, as can be encountered with antigen delivery using live vectors, can be virtually eliminated by employing the compositions or methods according to the subject invention. Unlike live vector delivery, the subject invention can provide a further advantage in that the DNA or RNA does not replicate in the host, but remains episomal with gene expression directed for as long as 19 months post-injection (Wolff, J. A., J. J. Ludike, G. Acsadi, P. Williams, A. Jani [1992] *Hum. Mol. Genet.* 1:363). A complete immune response can be obtained as recombinant antigen is synthesized intracellularly and presented to the host immune system in the context of autologous class I and class II MHC molecules.

As described, the subject invention concerns nucleic acids and compositions comprising those nucleic acids that can be effective in protecting an animal from disease or death caused by rickettsia. For example, a nucleic acid vaccine of the subject invention has been shown to be protective against *Cowdria ruminantium*, the causative agent of heartwater in domestic ruminants. Accordingly, DNA sequences of rickettsial genes, e.g., MAP1 or homologues thereof, can be useful as nucleic acid vaccines against human and animal rickettsial diseases. The MAP1 gene used to obtain this protection is also present in other rickettsiae including *Anaplasma marginale, Ehrlichia canis,* and in a causative agent of human ehrlichiosis, *Ehrlichia chaffeensis* (van Vliet, A., F. Jongejan, M. van Kleef, B. van der Zeijst [1994] *Infect. Immun* 62:1451). The MAP1 gene or a MAP1-like gene can also be found in certain *Rickettsia spp.* The MAP1-like gene from *Ehrlichia chaffeensis* has now been cloned and sequenced.

Compositions comprising the subject polynucleotides can include appropriate nucleic acid vaccine vectors (plasmids), which are commercially available (eg., Vical, San Diego, Calif.). In addition, the compositions can include a pharmaceutically acceptable carrier, e.g., saline. The pharmaceutically acceptable carriers are well known in the art and also are commercially available. For example, such acceptable carriers are described in E. W. Martin's *Remington's Phannaceutical Science,* Mack Publishing Company, Easton, Pa.

In a specific embodiment, the subject invention concerns a DNA vaccine (e.g., VCL1010/MAP1) containing the major antigenic protein 1 gene (MAP1) driven by the human cytomegalovirus (HCMV) enhancer-promoter injected intramuscularly into 8–10 week-old female DBA/2 mice after treating them with 50 μl/muscle of 0.5% bupivacaine 3 days previously. Up to 75% of the VCL1010/MAP1-immunized mice seroconverted and reacted with MAP1 in antigen blots. Splenocytes from immunized mice, but not from control mice immunized with VCL1010 DNA (plasmid vector, Vical, San Diego) proliferated in response to recombinant MAP1 and *C. ruminantium* antigens in in vitro lymphocyte proliferation tests. These proliferating cells from mice immunized with VCL1010/MAP1 DNA secreted IFN-gamma and IL-2 at concentrations ranging from 610 pg/ml and 152 pg/ml to 1290 pg/ml and 310 pg/ml, respectively. In experiments testing different VCL1010/MAP1 DNA vaccine dose regimens (25–100 µg/dose, 2 or 4 immunizations), survival rates of 23% to 88% (35/92 survivors/total in all VCL1010/MAP1 immunized groups) were observed on challenge with 30LD50 of C. ruminantium. Survival rates of 0% to 3% (1/144 survivors/total in all control groups) were recorded for control mice immunized similarly with VCL1010 DNA or saline. Accordingly, the subject invention concerns the discovery that the gene encoding the MAP1 protein can induce protective immunity as a DNA vaccine against rickettsial disease.

The nucleic acid sequences described herein have other uses, as well. For example, the nucleic acids of the subject invention can be useful as probes to identify complementary sequences within other nucleic acid molecules or genomes. Such use of probes can be applied to identify or distinguish infectious strains of organisms in diagnostic procedures or in rickettsial research where identification of particular organisms or strains is needed. As is well known in the art, probes can be made by labeling the nucleic acid sequences of interest according to accepted nucleic acid labeling procedures and techniques. A person of ordinary skill in the art would recognize that variations or fragments of the disclosed sequences which can specifically and selectively hybridize to the DNA of rickettsia can also function as a probe. It is within the ordinary skill of persons in the art, and does not require undue experimentation in view of the description provided herein, to determine whether a segment of the claimed DNA sequences is a fragment or variant which has characteristics of the full sequence, e.g., whether it specifically and selectively hybridizes or can confer protection against rickettsial infection in accordance with the subject invention. In addition, with the benefit of the subject disclosure describing the specific sequences, it is within the ordinary skill of those persons in the art to label hybridizing sequences to produce a probe.

It is also well known in the art that restriction enzymes can be used to obtain functional fragments of the subject DNA sequences. For example, Bal31 exonuclease can be conveniently used for time-controlled limited digestion of DNA (commonly referred to as "erase-a-base" procedures). See, for example, Maniatis et al (1982) *Molecular Cloning: A Laboratory Manual,* Cold Spring Harbor Laboratory, New York. See also Wei et al. (1983) *J. Biol. Chem.* 258:13006-13512.

In addition, the nucleic acid sequences of the subject invention can be used as molecular weight markers in nucleic acid analysis procedures.

Following are examples which illustrate procedures for practicing the invention. These examples should not be construed as limiting. All percentages are by weight and all solvent mixture proportions are by volume unless otherwise noted.

EXAMPLE 1

A nucleic acid vaccine construct was tested in animals for its ability to protect against death caused by infection with the rickettsia *Cowdria ruminantium.* The vaccine construct tested was the MAP1 gene of *C. ruminantium* inserted into plasmid VCL1010 (Vical, San Diego) under control of the human cytomegalovirus promoter-enhancer and intron A. In this study, seven groups containing 10 mice each were injected twice at 2-week intervals with either 100, 75, 50, or 25 µg VCL1010/MAP1 DNA (V/M in Table 1 below), or 100, 50 µg VCL1010 DNA (V in Table 1) or saline (Sal.), respectively. Two weeks after the last injections, 8 mice/group were challenged with 30LD50 of *C. ruminantium* and clinical symptoms and survival monitored. The remaining 2 mice/group were not challenged and were used for lymphocyte proliferation tests and cytokine measurements. The results of the study are summarized in Table 1, below:

TABLE 1

|  | 100 µg V/M | 75 µg V/M | 50 µg V/M | 25 µg V/M | 100 µg V | 50 µg V | Sal. |
|---|---|---|---|---|---|---|---|
| Survived | 5 | 7 | 5 | 3 | 0 | 0 | 0 |
| Died | 3 | 1 | 3 | 5 | 8 | 8 | 8 |

The VCL1010/MAP1 nucleic acid vaccine increased survival on challenge in all groups, with a total of 20/30 mice surviving compared to 0/24 in the control groups.

This study was repeated with another 6 groups, each containing 33 mice (a total of 198 mice). Three groups received 75 µg VCL1010/MAP1 DNA or VCL1010 DNA or saline (4 injections in all cases). Two weeks after the last injection, 30 mice/group were challenged with 30LD50 of *C. ruminantium* and 3 mice/group were sacrificed for lymphocyte proliferation tests and cytokine measurements. The results of this study are summarized in Table 2, below:

TABLE 2

|  | V/M 2 inj. | V 2 inj. | Sal. 2 inj. | V/M 4 inj. | V 4 inj. | Sal. 4 inj. |
|---|---|---|---|---|---|---|
| Survived | 7 | 0 | 0 | 8 | 0 | 1 |
| Died* | 23 | 30 | 30 | 22 | 30 | 29 |

*In mice that died in both V/M groups, there was an increase in mean survival time of approximately 4 days compared to the controls ($p < 0.05$).

Again, as summarized in Table 2, the VCL1010/MAP1 DNA vaccine increased the numbers of mice surviving in both immunized groups, although there was no apparent benefit of 2 additional injections. In these two experiments, there were a cumulative total of 35/92 (38%) surviving mice in groups receiving the VCL1010/MAP1 DNA vaccine compared to 1/144 (0.7%) surviving mice in the control groups. In both immunization and challenge trials described above, splenocytes from VCL1010/MAP1 immunized mice, but not from control mice, specifically proliferated to recombinant MAP1 protein and to *C. ruminantium* in lymphocyte proliferation tests. These proliferating splenocytes secreted IL-2 and gamma-interferon at concentrations up to 310 and 1290 pg/ml respectively. These data show that protection against rickettsial infections can be achieved with a DNA vaccine. In addition, these experiments show MAP1-related proteins as vaccine targets.

EXAMPLE 2

The MAP1 protein of *C. ruminantium* has significant similarity to MSP4 of *A. marginale,* and related molecules may also be presenting other rickettsial pathogens. To prove this, we used primers based on regions conserved between *C. ruminantium* and *A. marginale* in PCR to clone a MAP1-like gene from *E. chaffeensis.* The amino acid sequence derived from the cloned *E. chaffeensis* MAP1-like gene, and alignment with the corresponding genes of *C. ruminantium* and *A. marginale* is shown in FIG. 1. We have now identified the regions of MAP1-like genes which are highly conserved between *Ehrlichia, Cowdria,* and *Anaplasma* and which can allow cloning of the analogous genes from other rickettsiae.

It should be understood that the examples and embodiments described herein are for illustrative purposes only and that various modifications or changes in light thereof will be suggested to persons skilled in the art and are to be included within the spirit and purview of this application and the scope of the appended claims.

---

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 864 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 1..861

(xi) SEQUENCE DESCRIPTION: SEQ ID NO:1:

```
ATG AAT TGC AAG AAA ATT TTT ATC ACA AGT ACA CTA ATA TCA TTA GTG        48
Met Asn Cys Lys Lys Ile Phe Ile Thr Ser Thr Leu Ile Ser Leu Val
 1               5                  10                  15

TCA TTT TTA CCT GGT GTG TCC TTT TCT GAT GTA ATA CAG GAA GAC AGC        96
Ser Phe Leu Pro Gly Val Ser Phe Ser Asp Val Ile Gln Glu Asp Ser
                20                  25                  30

AAC CCA GCA GGC AGT GTT TAC ATT AGC GCA AAA TAC ATG CCA ACT GCA       144
Asn Pro Ala Gly Ser Val Tyr Ile Ser Ala Lys Tyr Met Pro Thr Ala
            35                  40                  45

TCA CAT TTT GGT AAA ATG TCA ATC AAA GAA GAT TCA AAA AAT ACT CAA       192
Ser His Phe Gly Lys Met Ser Ile Lys Glu Asp Ser Lys Asn Thr Gln
        50                  55                  60

ACG GTA TTT GGT CTA AAA AAA GAT TGG GAT GGC GTT AAA ACA CCA TCA       240
Thr Val Phe Gly Leu Lys Lys Asp Trp Asp Gly Val Lys Thr Pro Ser
 65                 70                  75                  80

GAT TCT AGC AAT ACT AAT TCT ACA ATT TTT ACT GAA AAA GAC TAT TCT       288
Asp Ser Ser Asn Thr Asn Ser Thr Ile Phe Thr Glu Lys Asp Tyr Ser
                85                  90                  95

TTC AGA TAT GAA AAC AAT CCG TTT TTA GGT TTC GCT GGA GCA ATT GGG       336
Phe Arg Tyr Glu Asn Asn Pro Phe Leu Gly Phe Ala Gly Ala Ile Gly
                100                 105                 110

TAC TCA ATG AAT GGA CCA AGA ATA GAG TTC GAA GTA TCC TAT GAA ACT       384
Tyr Ser Met Asn Gly Pro Arg Ile Glu Phe Glu Val Ser Tyr Glu Thr
            115                 120                 125

TTT GAT GTA AAA AAC CTA GGT GGC AAC TAT AAA AAC AAC GCA CAC ATG       432
Phe Asp Val Lys Asn Leu Gly Gly Asn Tyr Lys Asn Asn Ala His Met
        130                 135                 140

TAC TGT GCT TTA GAT ACA GCA GCA CAA AAT AGC ACT AAT GGC GCA GGA       480
Tyr Cys Ala Leu Asp Thr Ala Ala Gln Asn Ser Thr Asn Gly Ala Gly
145                 150                 155                 160

TTA ACT ACA TCT GTT ATG GTA AAA AAC GAA AAT TTA ACA AAT ATA TCA       528
Leu Thr Thr Ser Val Met Val Lys Asn Glu Asn Leu Thr Asn Ile Ser
                165                 170                 175

TTA ATG TTA AAT GCG TGT TAT GAT ATC ATG CTT GAT GGA ATA CCA GTT       576
Leu Met Leu Asn Ala Cys Tyr Asp Ile Met Leu Asp Gly Ile Pro Val
                180                 185                 190

TCT CCA TAT GTA TGT GCA GGT ATT GGC ACT GAC TTA GTG TCA GTA ATT       624
Ser Pro Tyr Val Cys Ala Gly Ile Gly Thr Asp Leu Val Ser Val Ile
```

```
                195                 200                 205
AAT GCT ACA AAT CCT AAA TTA TCT TAT CAA GGA AAG CTA GGC ATA AGT      672
Asn Ala Thr Asn Pro Lys Leu Ser Tyr Gln Gly Lys Leu Gly Ile Ser
        210                 215                 220

TAC TCA ATC AAT TCT GAA GCT TCT ATC TTT ATC GGT GGA CAT TTC CAT      720
Tyr Ser Ile Asn Ser Glu Ala Ser Ile Phe Ile Gly Gly His Phe His
225                 230                 235                 240

AGA GTT ATA GGT AAT GAA TTT AAA GAT ATT GCT ACC TTA AAA ATA TTT      768
Arg Val Ile Gly Asn Glu Phe Lys Asp Ile Ala Thr Leu Lys Ile Phe
            245                 250                 255

ACT TCA AAA ACA GGA ATA TCT AAT CCT GGC TTT GCA TCA GCA ACA CTT      816
Thr Ser Lys Thr Gly Ile Ser Asn Pro Gly Phe Ala Ser Ala Thr Leu
                260                 265                 270

GAT GTT TGT CAC TTT GGT ATA GAA ATT GGA GGA AGG TTT GTA TTT          861
Asp Val Cys His Phe Gly Ile Glu Ile Gly Gly Arg Phe Val Phe
                275                 280                 285

TAA                                                                  864
```

(2) INFORMATION FOR SEQ ID NO:2:

(i) SEQUENCE CHARACTERISTICS:
        (A) LENGTH: 287 amino acids
        (B) TYPE: amino acid
        (D) TOPOLOGY: linear (ii) MOLECULE TYPE: protein (xi) SEQUENCE DESCRIPTION: SEQ ID NO:2:

```
Met Asn Cys Lys Lys Ile Phe Ile Thr Ser Thr Leu Ile Ser Leu Val
 1               5                  10                  15

Ser Phe Leu Pro Gly Val Ser Phe Ser Asp Val Ile Gln Glu Asp Ser
                20                  25                  30

Asn Pro Ala Gly Ser Val Tyr Ile Ser Ala Lys Tyr Met Pro Thr Ala
            35                  40                  45

Ser His Phe Gly Lys Met Ser Ile Lys Glu Asp Ser Lys Asn Thr Gln
        50                  55                  60

Thr Val Phe Gly Leu Lys Lys Asp Trp Asp Gly Val Lys Thr Pro Ser
65                  70                  75                  80

Asp Ser Ser Asn Thr Asn Ser Thr Ile Phe Thr Glu Lys Asp Tyr Ser
                85                  90                  95

Phe Arg Tyr Glu Asn Asn Pro Phe Leu Gly Phe Ala Gly Ala Ile Gly
            100                 105                 110

Tyr Ser Met Asn Gly Pro Arg Ile Glu Phe Glu Val Ser Tyr Glu Thr
        115                 120                 125

Phe Asp Val Lys Asn Leu Gly Gly Asn Tyr Lys Asn Ala His Met
130                 135                 140

Tyr Cys Ala Leu Asp Thr Ala Ala Gln Asn Ser Thr Asn Gly Ala Gly
145                 150                 155                 160

Leu Thr Thr Ser Val Met Val Lys Asn Glu Asn Leu Thr Asn Ile Ser
                165                 170                 175

Leu Met Leu Asn Ala Cys Tyr Asp Ile Met Leu Asp Gly Ile Pro Val
            180                 185                 190

Ser Pro Tyr Val Cys Ala Gly Ile Gly Thr Asp Leu Val Ser Val Ile
        195                 200                 205

Asn Ala Thr Asn Pro Lys Leu Ser Tyr Gln Gly Lys Leu Gly Ile Ser
    210                 215                 220

Tyr Ser Ile Asn Ser Glu Ala Ser Ile Phe Ile Gly Gly His Phe His
```

```
                225                 230                 235                 240

Arg Val Ile Gly Asn Glu Phe Lys Asp Ile Ala Thr Leu Lys Ile Phe
                245                 250                 255

Thr Ser Lys Thr Gly Ile Ser Asn Pro Gly Phe Ala Ser Ala Thr Leu
                260                 265                 270

Asp Val Cys His Phe Gly Ile Glu Ile Gly Gly Arg Phe Val Phe
                275                 280             285
```

(2) INFORMATION FOR SEQ ID NO:3:

(i) SEQUENCE CHARACTERISTICS:
        (A) LENGTH: 842 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..840

(xi) SEQUENCE DESCRIPTION: SEQ ID NO:3:

```
ATG AAT TAC AAA AAA AGT TTC ATA ACA GCG ATT GAT ATC ATT AAT ATC      48
Met Asn Tyr Lys Lys Ser Phe Ile Thr Ala Ile Asp Ile Ile Asn Ile
                290                 295                 300

CTT CTC TTA CCT GGA GTA TCA TTT TCC GAC CCA AGG CAG GTA GTG GTC      96
Leu Leu Leu Pro Gly Val Ser Phe Ser Asp Pro Arg Gln Val Val Val
        305                 310                 315

ATT AAC GGT AAT TTC TAC ATC AGT GGA AAA TAC GAT GCC AAG GCT TCG     144
Ile Asn Gly Asn Phe Tyr Ile Ser Gly Lys Tyr Asp Ala Lys Ala Ser
320                 325                 330                 335

CAT TTT GGA GTA TTC TCT GCT AAG GAA GAA AGA AAT ACA ACA GTT GGA     192
His Phe Gly Val Phe Ser Ala Lys Glu Glu Arg Asn Thr Thr Val Gly
                340                 345                 350

GTG TTT GGA CTG AAG CAA AAT TGG GAC GGA AGC GCA ATA TCC AAC TCC     240
Val Phe Gly Leu Lys Gln Asn Trp Asp Gly Ser Ala Ile Ser Asn Ser
        355                 360                 365

TCC CCA AAC GAT GTA TTC ACT GTC TCA AAT TAT TCA TTT AAA TAT GAA     288
Ser Pro Asn Asp Val Phe Thr Val Ser Asn Tyr Ser Phe Lys Tyr Glu
370                 375                 380

AAC AAC CCG TTT TTA GGT TTT GCA GGA GCT ATT GGT TAC TCA ATG GAT     336
Asn Asn Pro Phe Leu Gly Phe Ala Gly Ala Ile Gly Tyr Ser Met Asp
            385                 390                 395

GGT CCA AGA ATA GAG CTT GAA GTA TCT TAT GAA ACA TTT GAT GTA AAA     384
Gly Pro Arg Ile Glu Leu Glu Val Ser Tyr Glu Thr Phe Asp Val Lys
400                 405                 410                 415

AAT CAA GGT AAC AAT TAT AAG AAT GAA GCA CAT AGA TAT TGT GCT CTA     432
Asn Gln Gly Asn Asn Tyr Lys Asn Glu Ala His Arg Tyr Cys Ala Leu
                420                 425                 430

TCC CAT AAC TCA GCA GCA GAC ATG AGT AGT GCA AGT AAT AAT TTT GTC     480
Ser His Asn Ser Ala Ala Asp Met Ser Ser Ala Ser Asn Asn Phe Val
            435                 440                 445

TTT CTA AAA AAT GAA GGA TTA CTT GAC ATA TCA TTT ATG CTG AAC GCA     528
Phe Leu Lys Asn Glu Gly Leu Leu Asp Ile Ser Phe Met Leu Asn Ala
        450                 455                 460

TGC TAT GAC GTA GTA GGC GAA GGC ATA CCT TTT TCT CCT TAT ATA TGC     576
Cys Tyr Asp Val Val Gly Glu Gly Ile Pro Phe Ser Pro Tyr Ile Cys
465                 470                 475

GCA GGT ATC GGT ACT GAT TTA GTA TCC ATG TTT GAA GCT ACA AAT CCT     624
Ala Gly Ile Gly Thr Asp Leu Val Ser Met Phe Glu Ala Thr Asn Pro
480                 485                 490                 495
```

```
AAA ATT TCT TAC CAA GGA AAG TTA GGT TTA AGC TAC TCT ATA AGC CCA        672
Lys Ile Ser Tyr Gln Gly Lys Leu Gly Leu Ser Tyr Ser Ile Ser Pro
            500                 505                 510

GAA GCT TCT GTG TTT ATT GGT GGG CAC TTT CAT AAG GTA ATA GGG AAC        720
Glu Ala Ser Val Phe Ile Gly Gly His Phe His Lys Val Ile Gly Asn
            515                 520                 525

GAA TTT AGA GAT ATT CCT ACT ATA ATA CCT ACT GGA TCA ACA CTT GCA        768
Glu Phe Arg Asp Ile Pro Thr Ile Ile Pro Thr Gly Ser Thr Leu Ala
            530                 535                 540

GGA AAA GGA AAC TAC CCT GCA ATA GTA ATA CTG GAT GTA TGC CAC TTT        816
Gly Lys Gly Asn Tyr Pro Ala Ile Val Ile Leu Asp Val Cys His Phe
545                 550                 555

GGA ATA GAA ATG GGA GGA AGG TTT AA                                     842
Gly Ile Glu Met Gly Gly Arg Phe
560                 565

(2) INFORMATION FOR SEQ ID NO:4:

(i) SEQUENCE CHARACTERISTICS:
        (A) LENGTH: 280 amino acids
        (B) TYPE: amino acid
        (D) TOPOLOGY: linear (ii) MOLECULE TYPE: protein (xi) SEQUENCE DESCRIPTION: SEQ ID NO:4:

Met Asn Tyr Lys Lys Ser Phe Ile Thr Ala Ile Asp Ile Ile Asn Ile
 1               5                  10                  15

Leu Leu Leu Pro Gly Val Ser Phe Ser Asp Pro Arg Gln Val Val Val
             20                  25                  30

Ile Asn Gly Asn Phe Tyr Ile Ser Gly Lys Tyr Asp Ala Lys Ala Ser
         35                  40                  45

His Phe Gly Val Phe Ser Ala Lys Glu Glu Arg Asn Thr Thr Val Gly
     50                  55                  60

Val Phe Gly Leu Lys Gln Asn Trp Asp Gly Ser Ala Ile Ser Asn Ser
65                  70                  75                  80

Ser Pro Asn Asp Val Phe Thr Val Ser Asn Tyr Ser Phe Lys Tyr Glu
                 85                  90                  95

Asn Asn Pro Phe Leu Gly Phe Ala Gly Ala Ile Gly Tyr Ser Met Asp
                100                 105                 110

Gly Pro Arg Ile Glu Leu Glu Val Ser Tyr Glu Thr Phe Asp Val Lys
            115                 120                 125

Asn Gln Gly Asn Asn Tyr Lys Asn Glu Ala His Arg Tyr Cys Ala Leu
        130                 135                 140

Ser His Asn Ser Ala Ala Asp Met Ser Ser Ala Ser Asn Asn Phe Val
145                 150                 155                 160

Phe Leu Lys Asn Glu Gly Leu Leu Asp Ile Ser Phe Met Leu Asn Ala
                165                 170                 175

Cys Tyr Asp Val Val Gly Glu Gly Ile Pro Phe Ser Pro Tyr Ile Cys
                180                 185                 190

Ala Gly Ile Gly Thr Asp Leu Val Ser Met Phe Glu Ala Thr Asn Pro
            195                 200                 205

Lys Ile Ser Tyr Gln Gly Lys Leu Gly Leu Ser Tyr Ser Ile Ser Pro
        210                 215                 220

Glu Ala Ser Val Phe Ile Gly Gly His Phe His Lys Val Ile Gly Asn
225                 230                 235                 240

Glu Phe Arg Asp Ile Pro Thr Ile Ile Pro Thr Gly Ser Thr Leu Ala
```

```
                       245                 250                 255
Gly Lys Gly Asn Tyr Pro Ala Ile Val Ile Leu Asp Val Cys His Phe
                260                 265                 270

Gly Ile Glu Met Gly Gly Arg Phe
            275                 280
```

(2) INFORMATION FOR SEQ ID NO:5:

(i) SEQUENCE CHARACTERISTICS:
        (A) LENGTH: 849 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..846

(xi) SEQUENCE DESCRIPTION: SEQ ID NO:5:

```
ATG AAT TAC AGA GAA TTG TTT ACA GGG GGC CTG TCA GCA GCC ACA GTC         48
Met Asn Tyr Arg Glu Leu Phe Thr Gly Gly Leu Ser Ala Ala Thr Val
                285                 290                 295

TGC GCC TGC TCC CTA CTT GTT AGT GGG GCC GTA GTG GCA TCT CCC ATG         96
Cys Ala Cys Ser Leu Leu Val Ser Gly Ala Val Val Ala Ser Pro Met
            300                 305                 310

AGT CAC GAA GTG GCT TCT GAA GGG GGA GTA ATG GGA GGT AGC TTT TAC        144
Ser His Glu Val Ala Ser Glu Gly Gly Val Met Gly Gly Ser Phe Tyr
        315                 320                 325

GTG GGT GCG GCC TAC AGC CCA GCA TTT CCT TCT GTT ACC TCG TTC GAC        192
Val Gly Ala Ala Tyr Ser Pro Ala Phe Pro Ser Val Thr Ser Phe Asp
    330                 335                 340

ATG CGT GAG TCA AGC AAA GAG ACC TCA TAC GTT AGA GGC TAT GAC AAG        240
Met Arg Glu Ser Ser Lys Glu Thr Ser Tyr Val Arg Gly Tyr Asp Lys
345                 350                 355                 360

AGC ATT GCA ACG ATT GAT GTG AGT GTG CCA GCA AAC TTT TCC AAA TCT        288
Ser Ile Ala Thr Ile Asp Val Ser Val Pro Ala Asn Phe Ser Lys Ser
                365                 370                 375

GGC TAC ACT TTT GCC TTC TCT AAA AAC TTA ATC ACG TCT TTC GAC GGC        336
Gly Tyr Thr Phe Ala Phe Ser Lys Asn Leu Ile Thr Ser Phe Asp Gly
            380                 385                 390

GCT GTG GGA TAT TCT CTG GGA GGA GCC AGA GTG GAA TTG GAA GCG AGC        384
Ala Val Gly Tyr Ser Leu Gly Gly Ala Arg Val Glu Leu Glu Ala Ser
        395                 400                 405

TAC AGA AGG TTT GCT ACT TTG GCG GAC GGG CAG TAC GCA AAA AGT GGT        432
Tyr Arg Arg Phe Ala Thr Leu Ala Asp Gly Gln Tyr Ala Lys Ser Gly
    410                 415                 420

GCG GAA TCT CTG GCA GCT ATT ACC CGC GAC GCT AAC ATT ACT GAG ACC        480
Ala Glu Ser Leu Ala Ala Ile Thr Arg Asp Ala Asn Ile Thr Glu Thr
425                 430                 435                 440

AAT TAC TTC GTA GTC AAA ATT GAT GAA ATC ACA AAC ACC TCA GTC ATG        528
Asn Tyr Phe Val Val Lys Ile Asp Glu Ile Thr Asn Thr Ser Val Met
                445                 450                 455

TTA AAT GGC TGC TAT GAC GTG CTG CAC ACA GAT TTA CCT GTG TCC CCG        576
Leu Asn Gly Cys Tyr Asp Val Leu His Thr Asp Leu Pro Val Ser Pro
            460                 465                 470

TAT GTA TGT GCC GGG ATA GGC GCA AGC TTT GTT GAC ATC TCT AAG CAA        624
Tyr Val Cys Ala Gly Ile Gly Ala Ser Phe Val Asp Ile Ser Lys Gln
        475                 480                 485

GTA ACC ACA AAG CTG GCC TAC AGG GGC AAG GTT GGG ATT AGC TAC CAG        672
Val Thr Thr Lys Leu Ala Tyr Arg Gly Lys Val Gly Ile Ser Tyr Gln
```

```
                490                 495                 500
TTT ACT CCG GAA ATA TCC TTG GTG GCA GGT GGG TTC TAC CAC GGG CTA         720
Phe Thr Pro Glu Ile Ser Leu Val Ala Gly Gly Phe Tyr His Gly Leu
505                 510                 515                 520

TTT GAT GAG TCT TAC AAG GAC ATT CCC GCA CAC AAC AGT GTA AAG TTC         768
Phe Asp Glu Ser Tyr Lys Asp Ile Pro Ala His Asn Ser Val Lys Phe
                    525                 530                 535

TCT GGA GAA GCA AAA GCC TCA GTC AAA GCG CAT ATT GCT GAC TAC GGC         816
Ser Gly Glu Ala Lys Ala Ser Val Lys Ala His Ile Ala Asp Tyr Gly
                540                 545                 550

TTT AAC CTT GGA GCA AGA TTC CTG TTC AGC TAA                             849
Phe Asn Leu Gly Ala Arg Phe Leu Phe Ser
555                 560
```

(2) INFORMATION FOR SEQ ID NO:6:

(i) SEQUENCE CHARACTERISTICS:
        (A) LENGTH: 282 amino acids
        (B) TYPE: amino acid
        (D) TOPOLOGY: linear (ii) MOLECULE TYPE: protein (xi) SEQUENCE DESCRIPTION: SEQ ID NO:6:

```
Met Asn Tyr Arg Glu Leu Phe Thr Gly Gly Leu Ser Ala Ala Thr Val
1               5                   10                  15

Cys Ala Cys Ser Leu Leu Val Ser Gly Ala Val Ala Ser Pro Met
                20                  25                  30

Ser His Glu Val Ala Ser Glu Gly Gly Val Met Gly Gly Ser Phe Tyr
                35                  40                  45

Val Gly Ala Ala Tyr Ser Pro Ala Phe Pro Ser Val Thr Ser Phe Asp
    50                  55                  60

Met Arg Glu Ser Ser Lys Glu Thr Ser Tyr Val Arg Gly Tyr Asp Lys
65                  70                  75                  80

Ser Ile Ala Thr Ile Asp Val Ser Val Pro Ala Asn Phe Ser Lys Ser
                85                  90                  95

Gly Tyr Thr Phe Ala Phe Ser Lys Asn Leu Ile Thr Ser Phe Asp Gly
                100                 105                 110

Ala Val Gly Tyr Ser Leu Gly Gly Ala Arg Val Glu Leu Glu Ala Ser
                115                 120                 125

Tyr Arg Arg Phe Ala Thr Leu Ala Asp Gly Gln Tyr Ala Lys Ser Gly
            130                 135                 140

Ala Glu Ser Leu Ala Ala Ile Thr Arg Asp Ala Asn Ile Thr Glu Thr
145                 150                 155                 160

Asn Tyr Phe Val Val Lys Ile Asp Glu Ile Thr Asn Thr Ser Val Met
                165                 170                 175

Leu Asn Gly Cys Tyr Asp Val Leu His Thr Asp Leu Pro Val Ser Pro
                180                 185                 190

Tyr Val Cys Ala Gly Ile Gly Ala Ser Phe Val Asp Ile Ser Lys Gln
                195                 200                 205

Val Thr Thr Lys Leu Ala Tyr Arg Gly Lys Val Gly Ile Ser Tyr Gln
            210                 215                 220

Phe Thr Pro Glu Ile Ser Leu Val Ala Gly Gly Phe Tyr His Gly Leu
225                 230                 235                 240

Phe Asp Glu Ser Tyr Lys Asp Ile Pro Ala His Asn Ser Val Lys Phe
                245                 250                 255

Ser Gly Glu Ala Lys Ala Ser Val Lys Ala His Ile Ala Asp Tyr Gly
```

-continued

```
                260                 265                 270
Phe Asn Leu Gly Ala Arg Phe Leu Phe Ser
            275                 280
```

We claim:

1. A composition comprising an isolated polynucleotide which encodes a polypeptide having the characteristic of eliciting an immune response protective against disease or death caused by a rickettsial pathogen wherein said polynucleotide has the nucleic acid sequence shown in SEQ ID NO. 1.

2. The composition, according to claim 1, wherein said polynucleotide is operably linked to a vector suitable for use in vaccination.

3. The composition, according to claim 1, further comprising a pharmaceutically acceptable carrier.

* * * * *

UNITED STATES PATENT AND TRADEMARK OFFICE
CERTIFICATE OF CORRECTION

PATENT NO. : 6,025,338

DATED : February 15, 2000

INVENTOR(S) : Anthony F. Barbet, Roman Reddy Ganta, Michael J. Burridge, Suman M. Mahan, Travis C. McGuire, Aceme Nyika, and Fred Rurangirwa It is certified that error appears in the above-identified patent and that said Letters Patent is hereby corrected as shown below:

Title Page [75] Inventors: "Anthony F. Barbet, Archer; Roman Reddy Ganta; Michael J. Burridge, both of Gainesville, all of Florida; Suman M. Mahan, Harare, Zimbabwe" should read --Anthony F. Barbet, Archer; Roman Reddy Ganta; Michael J. Burridge, both of Gainesville, all of Florida; Suman M. Mahan, Harare, Zimbabwe; Travis C. McGuire, Pullman, WA; Aceme Nyika, Harare, Zimbabwe; and Fred R. Rurangirwa, Pullman, WA.--.

Column 2, line 66: "(CIL)" should read --(CTL)--.

Column 4, lines 53-54: "Phannaceutical" should read --Pharmaceutical--.

Signed and Sealed this

First Day of May, 2001

Attest:

NICHOLAS P. GODICI

Attesting Officer

Acting Director of the United States Patent and Trademark Office